(12) United States Patent
Janssens

(10) Patent No.: US 9,050,071 B2
(45) Date of Patent: Jun. 9, 2015

(54) INSTRUMENT FOR TAKING A TISSUE SAMPLE

(71) Applicant: Phillibert Jacques Janssens, Hasselt (BE)

(72) Inventor: Phillibert Jacques Janssens, Hasselt (BE)

(*) Notice: Subject to any disclaimer, the term of this patent is extended or adjusted under 35 U.S.C. 154(b) by 149 days.

(21) Appl. No.: 13/753,803

(22) Filed: Jan. 30, 2013

(65) Prior Publication Data

US 2013/0197395 A1    Aug. 1, 2013

(30) Foreign Application Priority Data

Feb. 1, 2012 (BE) .................................. 2012/0062

(51) Int. Cl.
*A61B 10/00* (2006.01)
*A61B 10/02* (2006.01)
*A61B 17/32* (2006.01)
*A61B 17/3205* (2006.01)

(52) U.S. Cl.
CPC ............. *A61B 10/02* (2013.01); *A61B 10/0266* (2013.01); *A61B 2017/320064* (2013.01); *A61B 17/32053* (2013.01)

(58) Field of Classification Search
CPC ....................................................... A61B 10/02
USPC .................. 600/562–567, 104, 114; 604/164; 606/167
See application file for complete search history.

(56) References Cited

U.S. PATENT DOCUMENTS

| | | | |
|---|---|---|---|
| 2,850,007 A | 9/1958 | Lingley | |
| 3,683,891 A | 8/1972 | Eskridge et al. | |
| 5,488,958 A | 2/1996 | Topel et al. | |
| 6,007,481 A * | 12/1999 | Riek et al. | 600/114 |
| 6,083,237 A | 7/2000 | Huitema et al. | |

FOREIGN PATENT DOCUMENTS

| | | |
|---|---|---|
| RU | 401360 | 11/1974 |
| WO | 02/065919 A1 | 8/2002 |

OTHER PUBLICATIONS

European Search Report for EP 13 00 0318, dated Apr. 8, 2013.

* cited by examiner

*Primary Examiner* — Brian Szmal
(74) *Attorney, Agent, or Firm* — Bacon & Thomas, PLLC

(57) ABSTRACT

An instrument for taking a tissue sample includes a tissue receiving element with a distal end and a proximal end and at least partly has a spiral or helix that has an outer surface and a central longitudinal axis (X-X'). The spiral or helix has at least has one zone where the distance ($d_d$) from the outer surface to the central longitudinal axis (X-X') is smaller than at a more proximally located part of the spiral or helix.

3 Claims, 5 Drawing Sheets

INSTRUMENT FOR TAKING A TISSUE SAMPLE

FIELD OF INVENTION

The present invention relates to an instrument for taking a tissue sample.

BACKGROUND

More specifically it concerns an instrument of the type described in WO 02/065919, in which a spiral or helical tissue receiving element is turned in the tissue from which a sample must be taken, after which the tissue around this tissue receiving element is cut with a sharp cannula around the tissue receiving element and is torn off at the distal end of the tissue receiving element, thereby obtaining a tissue sample in the tissue receiving element. However, this known instrument has a number of disadvantages. They are related to the fibres in the various tissues.

The organs in human and animal bodies have fibres of connective tissue. They give structure to the organ, which normally speaking additionally consist of soft, unstructured tissue. These fibres in organs can run in relatively arbitrary directions or can have one or more primary directions.

It has turned out that, when the tissue to be sampled has 'unifrontal' fibres that enter the cut tissue via the frontal connection of the sample to the rest of the tissue, thus where the tissue has to tear loose, and similar fibres that make a curve in order to recede in the same direction, also via this frontal connection, the 'bifrontal' fibres, it can happen that the force exerted by the known spiral or helical tissue receiving element is not great enough to tear off these fibres.

As a result it may happen that during the biopsy, the intended tissue sample, that is in the tissue receiving element, is not torn loose from the other tissue and isolated as a sample, but instead of this, while the tissue receiving element is withdrawn from the tissue, the intended sample remains attached to the organ and thus slides out of the receiving space.

When unifrontal fibres are present, but even more so with the presence of lateral fibres, which extend partly transverse to the longitudinal direction of the tissue receiving element and thus protrude through the space between the windings of the spiral or helical tissue receiving element, there is also the disadvantage that the sharp cannula partially pushes the fibres along during the cutting movement, instead of cutting through them, and that these fibres accumulate in the very limited space between the tissue receiving element and the cannula, and thereby impede the movement of the cannula or even make it impossible.

This results in the tissue samples not being cut well, if at all.

Certainly when taking samples from relatively hard tissues, the spiral or helical tissue receiving element can also expand due to the forces acting on it, such that the desired movement of the cannula is hampered or rendered impossible.

It is known, for example in U.S. Pat. No. 6,083,237, to narrow the point, thus the distal end, over a short length, i.e. a maximum of one winding of such a spiral, in order to enable easier penetration into the tissue.

This has the disadvantage that this narrowed point, during insertion, damages the tissue that will later serve as a sample, so that taking an undamaged sample of a certain size is difficult.

SUMMARY

The purpose of the present invention is to provide a solution to at least one of the aforementioned and other disadvantages, by providing an instrument for taking a tissue sample, that comprises a tissue receiving element with a distal end and a proximal end and at least partly consists of a spiral or helix that has an outer surface and which has a central longitudinal axis, whereby the spiral or helix has at least has one zone where the distance from the outer surface to the central longitudinal axis is smaller than at a more proximally located part of the spiral or helix, whereby the zone runs from the distal end in the direction of the proximal end over a distance of at least one complete winding of the spiral or helix.

This means that the zone at least partly extends in the region of the spiral or helix that is intended to be surrounded by the cannula during a sampling procedure, and to exert a cutting effect together with this cannula during this procedure.

This has the advantage that there is space for unifrontal fibres in the tissue to protrude outside the tissue receiving element, even after the cutting by a cannula, such that the pulling force exerted by the physician on the instrument can be more effectively transmitted to the tissue, so that the tissue tears off, as desired. This effect is of course much greater with bifrontal fibres, which can be located around the windings of the tissue receiving element, and on which a much greater force can thus be exerted.

This means that the risk of the instrument being extracted from the tissue without a significant sample being taken is reduced.

As a result, on the part where the distance from the outer surface to the central longitudinal axis is smaller, there is space for the fibres that have not been cut through to accumulate, such that the cutting movement is impeded less or not at all.

This configuration of the tissue receiving element also provides space to accommodate any expansion of the tissue receiving element without disturbing the cutting movement.

It is self-evident that these effects are greater as the zone, over which the distance from the outer surface to the central longitudinal axis is smaller than at a more proximal part of the spiral or helix, extends over a greater proportion of the tissue receiving element, and at least extends to the section of the spiral or helix that is intended to have a cutting effect together with the cannula, thus the section over which the cannula slides during normal usage.

In a preferred embodiment that is why the said zone runs from the distal end in the direction of the proximal end over a distance that corresponds to at least two full windings, more preferably over at least half of the length of the spiral or helix, or even over the entire length of the spiral or helix.

In a preferred embodiment, along an intersecting line between the outer surface and a plane of which the central longitudinal axis forms part, where this intersecting line runs through the zone, at every position, the distance from the outer surface to the central longitudinal axis is less than or equal to the distance from the outer surface to the central longitudinal axis at every more proximal position along the intersecting line. More preferably the distance from the outer surface to the central longitudinal axis is less than the distance from the outer surface to the central longitudinal axis at every more proximal position along the intersecting line.

In a further preferred embodiment the distance from the outer surface to the central longitudinal axis at the distal end is smaller than at the proximal end, viewed along the intersecting line of the outer surface with every plane of which the central longitudinal axis forms part.

In another further preferred embodiment the spiral or helix has an inner surface, whereby that inner surface, viewed from the distal end, defines the shape of a geometrical cylinder.

This means that the inside space has a constant diameter over a certain distance from the distal end, or even over the entire length of the spiral, and thus does not narrow near the point.

This means that the thickness of the body that forms the spiral or helix is smaller near the distal end than near the proximal end.

In this way sufficient space remains centrally in the tissue receiving element to take an undamaged sample of the desired size.

This also prevents the action of inserting the spiral leading to damage of the tissue that is taken as a sample.

In a further preferred embodiment the instrument also comprises a tubular cutting element that has a distal end with a cutting edge and which fits around the tissue receiving element. This cutting edge can take on different forms, such as flat, toothed, etc.

BRIEF DESCRIPTION OF THE DRAWINGS

With the intention of better showing the characteristics of the invention, a preferred embodiment of an instrument according to the invention is described hereinafter by way of an example, without any limiting nature, with reference to the accompanying drawings, wherein.

DETAILED DESCRIPTION OF VARIOUS EMBODIMENTS OF THE DISCLOSURE

Figure 1:
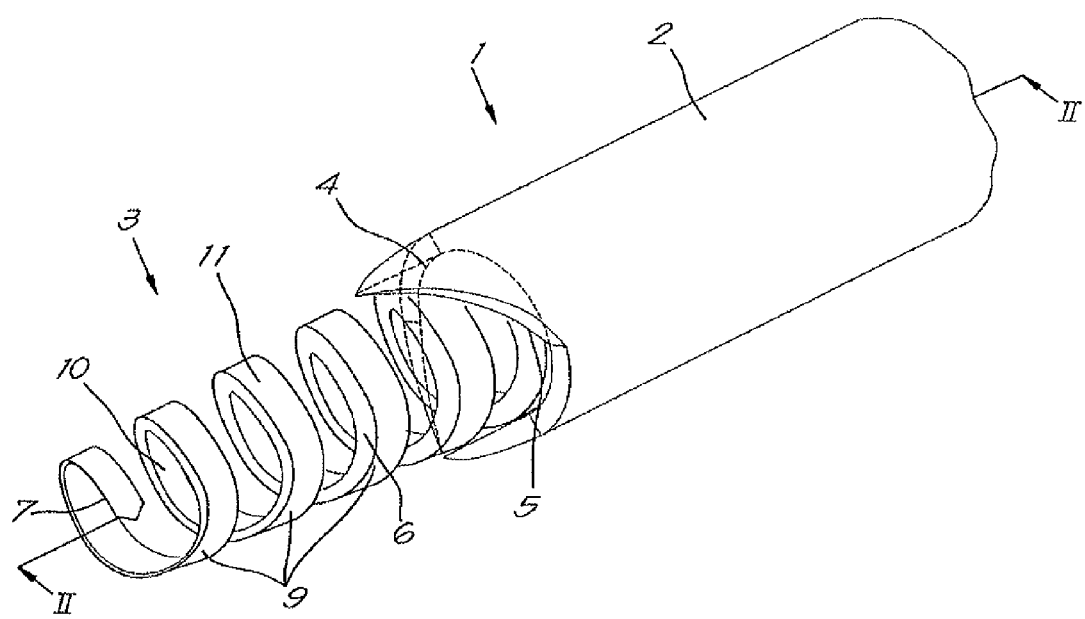
FIG. 1 schematically shows a perspective view of an instrument according to the invention.

The instrument 1 shown in FIGS. 1 to 5 comprises a tubular cutting element 2 and a tissue receiving element 3. The cutting element has a distal end 4 that has a sharp edge 5 suitable for cutting. The cutting element has an inside diameter $d_s$.

The tissue receiving element 3 is formed by a helically extending metal body 6 with a distal end 7 that is provided with a point that can penetrate the tissue and a proximal end 8.

In this case the helical body has six windings 9. The helix has a central longitudinal axis X-X', an inner surface 10 and an outer surface 11.

The inner surface 10 is hereby the surface of the helical body 6 that is turned towards the central longitudinal axis X-X'. The outer surface 11 is hereby the surface of the helical body 6 that is turned away from the central longitudinal axis X-X'.

The inner surface 10 has such a shape that it defines a cylindrical tissue receiving space 12 with a diameter $d_w$.

The outer surface 11 is such that for every successive winding 9, from proximal to distal, the distance from the outer surface 11 to the central longitudinal axis X-X' is smaller, in other words the thickness of the helical body 6 is smaller for each successive winding 9.

In this embodiment, but not necessarily, this is the case around the entire periphery of the helix, thus along the intersecting line of the outer surface 11 with every plane of which the central longitudinal axis X-X' forms part.

Figure 2:
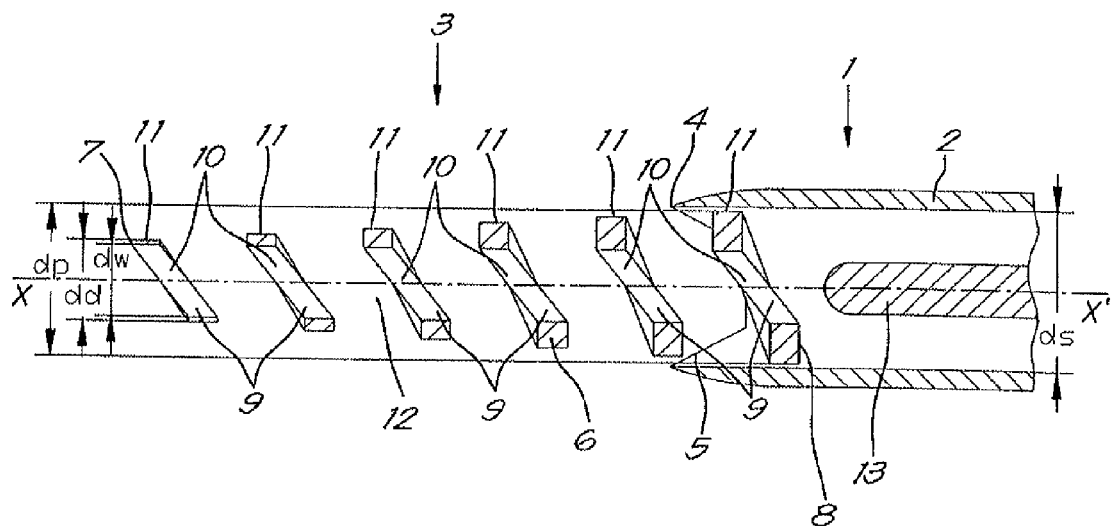
FIG. 2 shows a cross-section of the instrument of FIG. 1 along the line II-II.

Thus for the most distal winding 9, as is clear from FIG. 2, the outer surface 11 is located at a distance of $0.5*d_d$ from the central longitudinal axis X-X', while it is a distance of $0.5*d_p$ for the most proximal winding.

The tissue receiving element 3 is connected by means of a shaft 13 to a handle (not shown) in order to give a movement to the shaft 13 and thereby to the tissue receiving element 3.

The cutting element 2 can be made, for example, by taking a first tube, for example of metal, for example with an inside diameter of $d_s$ of 2 mm and providing it with a sharp edge 5.

The tissue receiving element 3 can be made for example by taking a second tube, for example of metal, with an outer diameter $d_p$ that is just less than the inside diameter $d_s$ of the first tube, and providing this second tube with a helical cut by means of a milling cutter for example, so that a metal helix remains.

In this example the tube and the rod are both made of metal, but they can also be made of different materials.

The difference between the outer diameter $d_p$ of the second tube and the inside diameter $d_s$ of the first tube is determined experimentally, because the combination of the tissue receiving element 3 and the cutting element 2 partly determine the cutting properties of the instrument 1 to be formed.

Then the windings 9 of the helix, going from one end, that will later become the proximal end 8, to the other end, which will later become the distal end 7, are ground away more per winding, so that a shape such as in FIGS. 1 to 5 is formed.

Then the tissue receiving element 3 thus formed is provided with a shaft 13 and the tissue receiving element 3 and the cutting element 2 are put together into the instrument 1.

An embodiment in which the shaft 13 is formed by a part of the second tube that is not provided with a helical cut is also possible.

The operation of the instrument according to the invention is simple and as follows.

First a localisation needle, a 'trocar' is inserted at the site where a tissue sample must be taken. Then the cutting element 2, the size that is adapted to the localisation needle, is slid over the localisation needle, also to the site where the tissue sample must be taken. The localisation needle is now withdrawn.

Then the tissue receiving element 3 is brought through the cutting element 2. Through a turning movement this tissue receiving element 3 is now turned in the tissue from which a sample must be taken. The tissue in the tissue receiving space 12 is thus not disturbed. This is the situation as shown in FIGS. 3, 4 and 5.

Then the cutting element 2 is slid in the distal direction P, whereby a rotation movement is made at the same time. Also through the interaction between the tissue receiving element 3 and the cutting element 2 the tissue is now cut loose around the tissue receiving element 3, as indicated in the drawings by line S.

Hereby there is some space between the cutting element 2 and the outer surface 11, primarily near the distal end 7.

Figure 3:
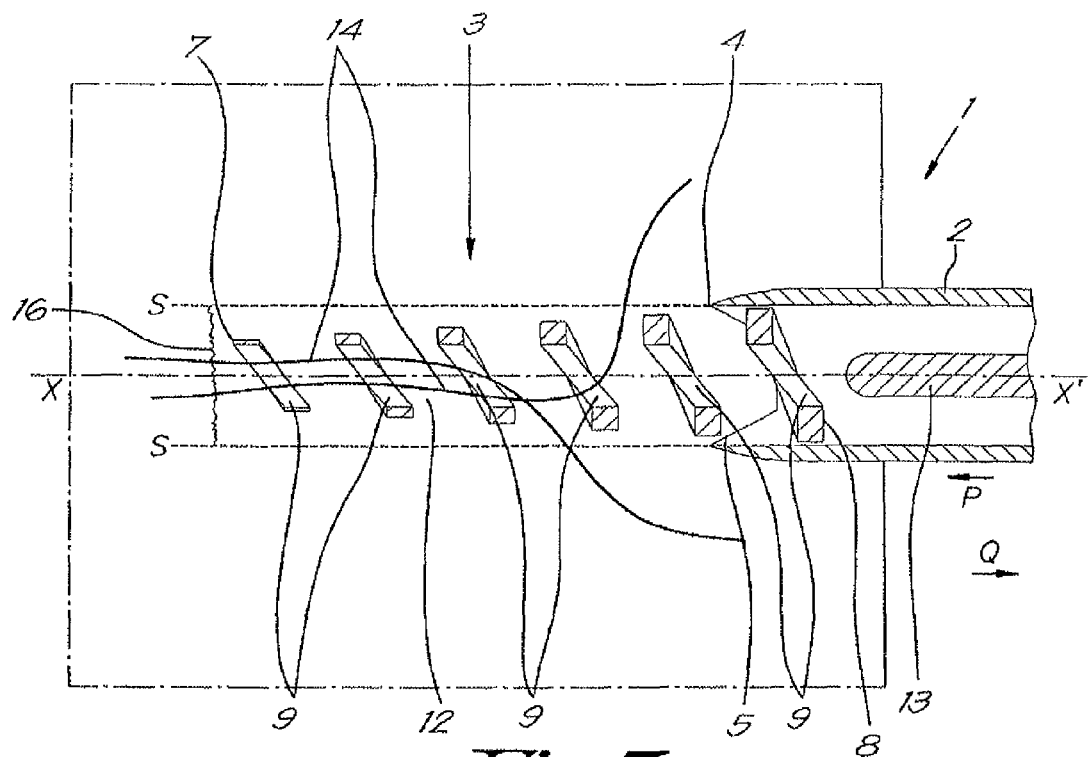
FIGS. 3 to 5 show the instrument of FIG. 2 during use in three different tissue types.
Figure 4:
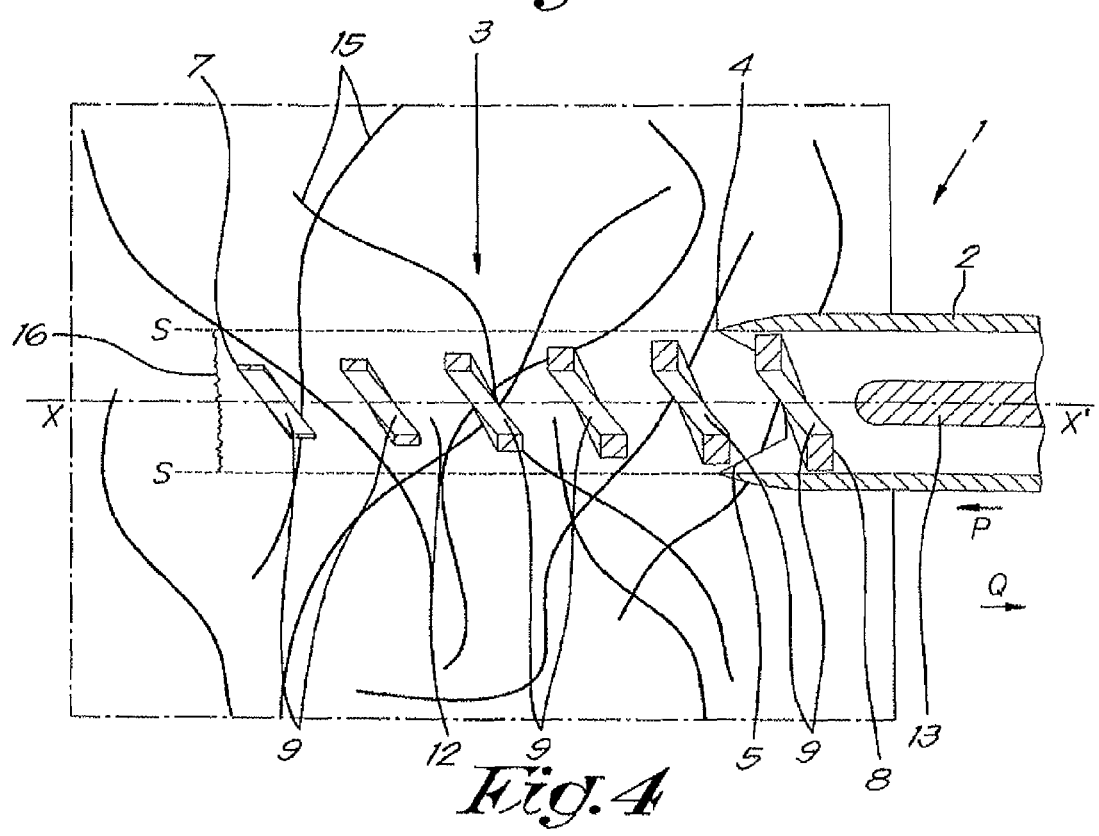
Figure 5:
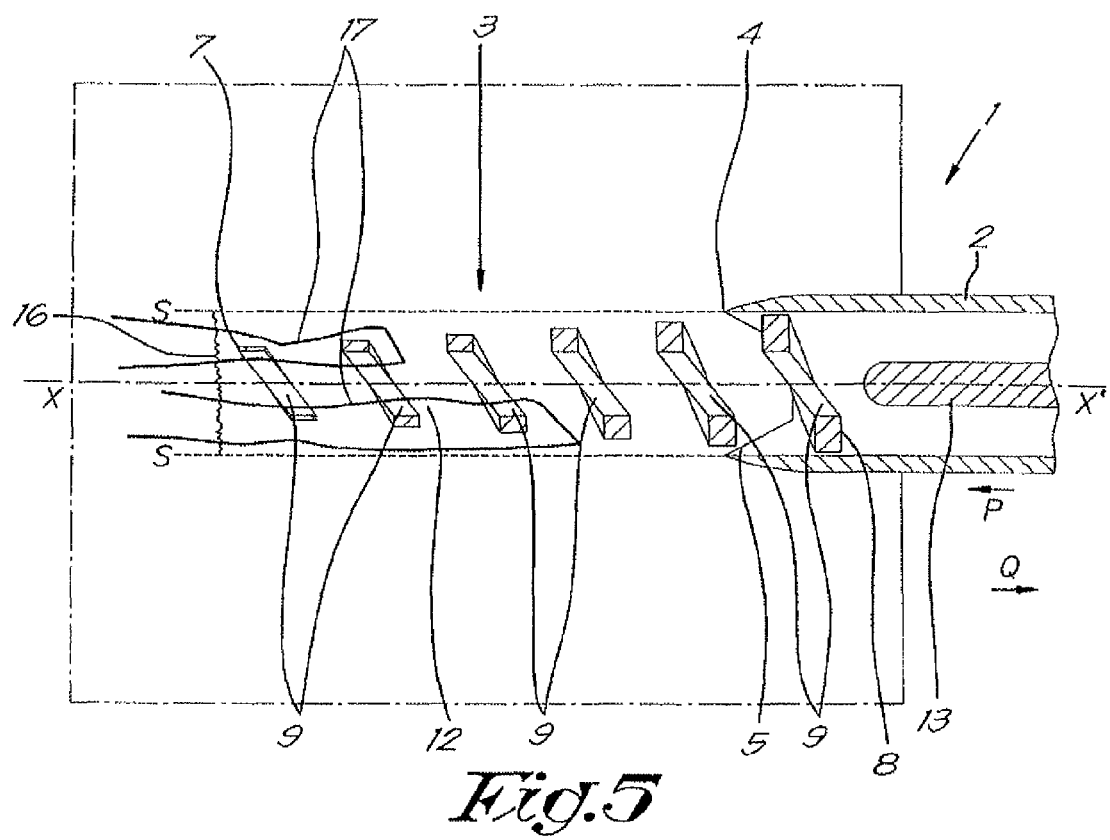

During cutting this space provides room for the parts of the unifrontal fibres 14, of which a part protrudes laterally outside the tissue receiving element 3, as shown in FIG. 3, or for the lateral fibres 15 that protrude outside the tissue receiving element 3, as shown in FIG. 4. As a result the cutting action is not disturbed or only to a limited extent.

Then a pulling force is exerted on the instrument 1 or receiving element 2 in the proximal direction Q. As a result the tissue sample tears away near the distal end 7 of the tissue receiving element 3, according to the tear line 16, and it can be taken outside the body of the patient for the necessary analyses.

Hereby the space between the outer surface 11 and the cut S is important, because this enables parts of the bifrontal fibres 17, after cutting, to protrude outside the tissue receiving element 3 without being cut off, so that a significant force can be exerted on the tissue sample by the physician, via the tissue receiving element 3, resulting in the tissue sample tearing away, and with little risk of sample loss when the tissue receiving element 3 is pulled entirely out of the tissue.

As shown in FIG. 5, thanks to the space between the outer surface 11 and the cut S, the bifrontal fibres 17 can flow back in a curve around the helical body 6, so that via these bifrontal fibres 17 a very large force can certainly be transmitted from the tissue receiving element 3 to the tissue.

Figure 6:
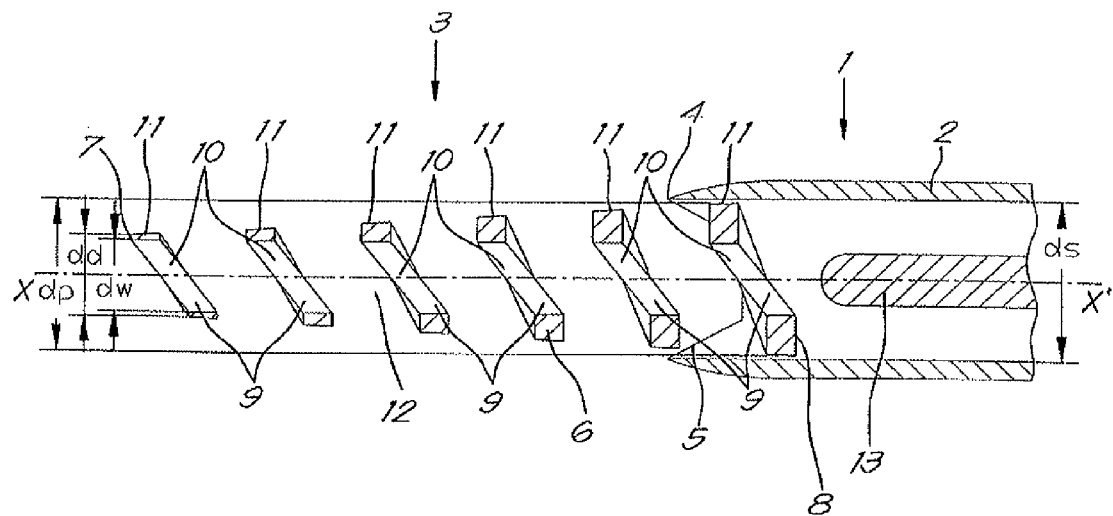
FIGS. 6 and 7 each show an alternative embodiment of the instrument according to the invention, in a cross-section as in FIG. 2.

The alternative instrument 1 of FIG. 6 differs from that of FIG. 2, because the outer surface 11 of each winding is not parallel to the central longitudinal axis X-X', but follows a straight line between the most distal winding 9 and the most proximal winding 9.

Figure 7:
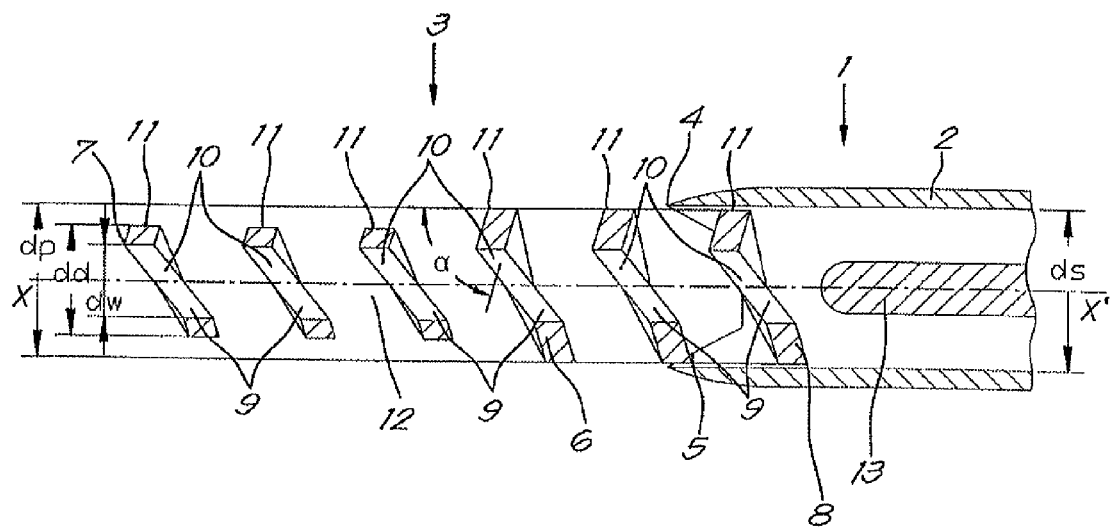

The alternative instrument 1 of FIG. 7 differs from that of FIG. 2 because the most distal windings 9 each have an outer surface 11 with a short distance $0.5*d_d$ to the central longitudinal axis X-X', which is the same for each of these windings. The most proximal windings also all have the same larger distance $0.5*dp$ to the central longitudinal axis X-X'.

The cross-section of the helical body 6 transverse to the direction in which the body extends helically, is also parallelogram-shaped, whereby the proximal and outermost angle α is acute.

Figure 8:
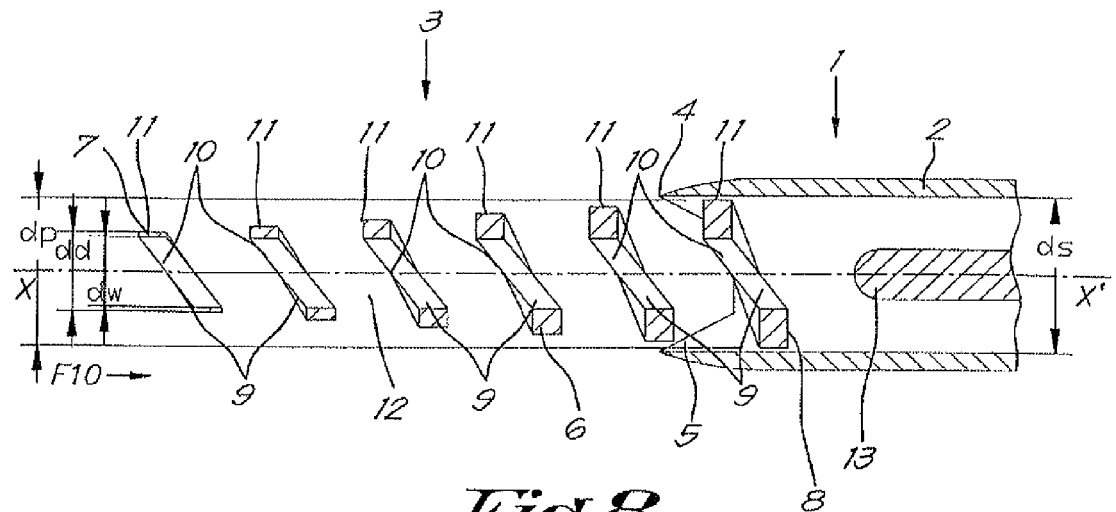
FIGS. 8 to 10 together show an alternative embodiment of the instrument according to the invention, whereby in FIG. 8 this is a cross-section as in FIG. 2, and in FIGS. 9 and 10 cross-sections perpendicular thereto.
Figure 9:
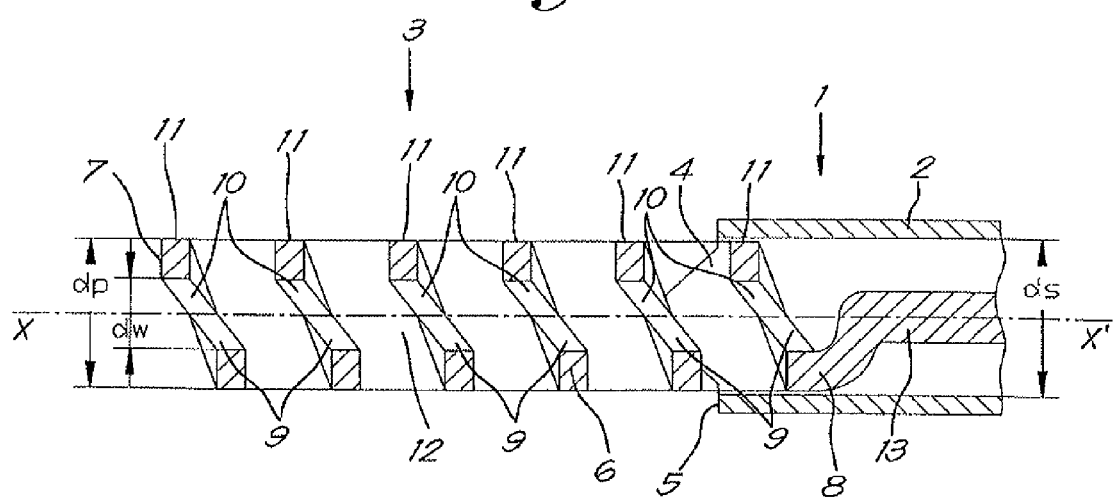
Figure 10:
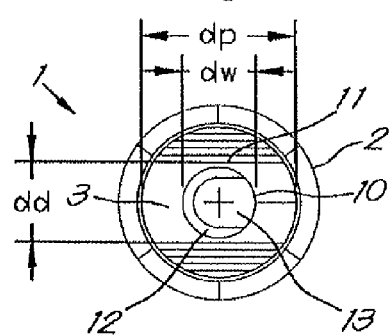

The alternative instrument of FIGS. 8 to 10 differs from the instruments 1 described earlier because the outer surface 11 of the tissue receiving element 3 only has a shorter distance to the central longitudinal axis X-X' than at the proximal end 8 over two zones extending parallel to the longitudinal axis X-X' at the distal end 7.

Outside these zones the entire outer surface 11, viewed over all windings 9 from distal to proximal, is straight over the entire length of the helical body 6, i.e. parallel to the central longitudinal axis X-X'.

The form of the outer surface 11 of the tissue receiving element 3, going from proximal to distal, in the above examples is shown as a linear or step function. However, other forms are also possible such as hyperbolic or parabolic, or combinations thereof.

It should be noted that in the drawings described above the differences in the diameters $d_p$ and $d_d$ are enlarged, for the purpose of better clarifying the invention. In a practical instrument, with a diameter $d_p$ of approximately 3 mm, the difference between $d_p$ and $d_s$ is approximately 10% of $d_p$, thus approximately 0.3 mm.

The present invention is by no means limited to the embodiments described as an example and shown in the drawings, but an instrument according to the invention can be realised in all kinds of variants, without departing from the scope of the invention.

The invention claimed is:

1. An instrument for taking a tissue sample, comprising:
a tissue receiving element having a distal end and a proximal end;
said element comprising a spiral or helix that has an outer surface and a central longitudinal axis;
said spiral or helix having at least one zone where the distance ($d_d$) from the outer surface to the central longitudinal axis (X-X') is smaller than at a more proximally located part of the spiral or helix, so that the zone runs from the distal end in the direction of the proximal end over a distance of at least one complete winding of the spiral or helix;
said spiral or helix having an inner surface wherein a distance ($d_w$) from said inner surface to the central longitudinal axis (X-X'), at every position in the zone or over at least a section of the zone that connects to the distal end, is equal to the distance ($d_w$) at every more distally located part of the spiral or helix; and
said spiral or helix being formed by a helical body wherein a thickness ($d_a$-$d_w$) of the helical body for every successive winding, going from the proximal end to the distal end, is smaller than for the previous windings.

2. The instrument according to claim 1, wherein the cross-section of the tissue receiving element transverse to the direction in which the spiral or helix extends spirally or helically, has a shape such that the most proximal and outermost angle (α) of this cross-section is acute.

3. The instrument according to claim 2, wherein the cross-section has a form of a parallelogram or triangle.

\* \* \* \* \*